United States Patent
Wang et al.

(10) Patent No.: US 7,975,537 B2
(45) Date of Patent: Jul. 12, 2011

(54) SYSTEMS AND METHODS FOR SENSING AN AMMONIA CONCENTRATION IN EXHAUST GASES

(75) Inventors: Da Yu Wang, Troy, MI (US); Sheng Yao, Macomb, MI (US)

(73) Assignee: Delphi Technologies, Inc., Troy, MI (US)

( * ) Notice: Subject to any disclaimer, the term of this patent is extended or adjusted under 35 U.S.C. 154(b) by 373 days.

(21) Appl. No.: 12/109,405

(22) Filed: Apr. 25, 2008

(65) Prior Publication Data
US 2009/0266142 A1  Oct. 29, 2009

(51) Int. Cl.
*G01M 15/10* (2006.01)

(52) U.S. Cl. ..................... 73/114.71; 73/23.32

(58) Field of Classification Search .............. 73/23.31, 73/114.71, 114.72, 23.32
See application file for complete search history.

(56) References Cited

U.S. PATENT DOCUMENTS

| | | | |
|---|---|---|---|
| 5,021,227 A * | 6/1991 | Kobayashi et al. | 423/212 |
| 5,116,579 A * | 5/1992 | Kobayashi et al. | 422/111 |
| 6,287,439 B1 * | 9/2001 | Kato et al. | 204/425 |
| 6,533,911 B1 * | 3/2003 | Fujita et al. | 204/424 |
| 6,544,405 B2 | 4/2003 | Clyde et al. | |
| 6,555,159 B2 | 4/2003 | Clyde et al. | |
| 6,571,601 B2 * | 6/2003 | Irion et al. | 73/23.31 |
| 6,694,724 B2 * | 2/2004 | Tanaka et al. | 60/274 |
| 6,787,776 B2 * | 9/2004 | Webber et al. | 250/341.2 |
| 6,882,929 B2 * | 4/2005 | Liang et al. | 701/115 |
| 7,074,319 B2 * | 7/2006 | Wang et al. | 205/780.5 |
| 7,150,145 B2 * | 12/2006 | Patchett et al. | 60/286 |
| 7,294,252 B2 * | 11/2007 | Wang et al. | 205/781 |
| 7,578,925 B2 * | 8/2009 | Kubinski et al. | 205/781 |
| 2003/0062264 A1 * | 4/2003 | Kitanoya et al. | 204/424 |
| 2004/0118703 A1 | 6/2004 | Wang et al. | |
| 2005/0252201 A1 * | 11/2005 | Lecea et al. | 60/286 |
| 2006/0151338 A1 * | 7/2006 | Wang et al. | 205/780.5 |
| 2007/0080074 A1 | 4/2007 | Wang et al. | |
| 2009/0084673 A1 * | 4/2009 | Ogata et al. | 204/243.1 |
| 2009/0139210 A1 * | 6/2009 | Sanchez | 60/276 |

* cited by examiner

*Primary Examiner* — Freddie Kirkland, III
(74) *Attorney, Agent, or Firm* — Thomas N. Twomey (57) ABSTRACT

Systems and methods for determining an $NH_3$ concentration in exhaust gases from an engine are provided. In one exemplary embodiment, a method includes generating a first signal from an $NH_3$ sensor fluidly communicating with the exhaust gases. The method further includes generating a second signal from an air humidity sensor disposed proximate to an air intake manifold of the engine indicating a humidity level. The method further includes determining an air/fuel ratio associated with the engine. The method further includes determining an $NH_3$ deviation value in a calibration table based on the second signal and the air/fuel ratio, utilizing a controller. The method further includes determining an $NH_3$ concentration value based on the first signal and the $NH_3$ deviation value, utilizing the controller. The $NH_3$ concentration value is indicative of the $NH_3$ concentration in the exhaust gases. The method further includes storing the $NH_3$ concentration value in a memory device, utilizing the controller.

6 Claims, 6 Drawing Sheets

| HUMIDITY [g/kg] EMF DEVIATION [mV] A/F RATIO | 0 | 3 | 7 | 10 | 15 | 20 | 25 | 30 | 35 | 40 | 45 | 50 | 55 | 60 | 65 |
|---|---|---|---|---|---|---|---|---|---|---|---|---|---|---|---|
| 20 | -2 | -4 | -6 | -7 | -9 | -11 | -13 | -14 | -16 | -17 | -18 | -19 | -20 | -21 | -22 |
| 25 | -3 | -5 | -7 | -9 | -11 | -14 | -16 | -18 | -20 | -22 | -23 | -25 | -26 | -27 | -29 |
| 30 | 0 | -3 | -6 | -8 | -11 | -14 | -16 | -18 | -21 | -23 | -24 | -26 | -28 | -29 | -31 |
| 35 | 3 | 0 | -3 | -6 | -9 | -13 | -15 | -18 | -20 | -23 | -25 | -26 | -28 | -30 | -31 |
| 40 | 6 | 3 | -1 | -4 | -8 | -11 | -14 | -17 | -20 | -22 | -24 | -26 | -28 | -30 | -32 |
| 45 | 9 | 5 | 1 | -2 | -6 | -10 | -14 | -17 | -19 | -22 | -24 | -26 | -28 | -30 | -32 |
| 50 | 12 | 8 | 3 | 0 | -5 | -9 | -13 | -16 | -19 | -21 | -24 | -26 | -28 | -30 | -32 |
| 55 | 14 | 10 | 5 | 1 | -4 | -8 | -12 | -15 | -18 | -21 | -23 | -26 | -28 | -30 | -32 |
| 60 | 17 | 12 | 6 | 3 | -2 | -7 | -11 | -14 | -18 | -20 | -23 | -25 | -28 | -30 | -32 |
| 65 | 19 | 14 | 8 | 4 | -1 | -6 | -10 | -14 | -17 | -20 | -23 | -25 | -27 | -30 | -31 |
| 70 | 22 | 16 | 10 | 5 | 0 | -5 | -10 | -13 | -17 | -20 | -22 | -25 | -27 | -29 | -31 |
| 75 | 24 | 18 | 11 | 7 | 1 | -3 | -9 | -13 | -16 | -19 | -22 | -25 | -27 | -29 | -31 |
| 80 | 26 | 19 | 12 | 8 | 1 | -4 | -8 | -12 | -16 | -19 | -22 | -25 | -27 | -29 | -31 |

| HUMIDITY [g/kg] EMF DEVIATION [mV] A/F RATIO | 0 | 3 | 7 | 10 | 15 | 20 | 25 | 30 | 35 | 40 | 45 | 50 | 55 | 60 | 65 |
|---|---|---|---|---|---|---|---|---|---|---|---|---|---|---|---|
| 20 | 1 | 6 | 4 | 3 | 1 | -1 | -2 | -4 | -5 | -7 | -8 | -9 | -10 | -11 | -12 |
| 25 | 7 | 6 | 3 | 1 | -1 | -4 | -6 | -8 | -10 | -11 | -13 | -14 | -16 | -17 | -18 |
| 30 | 10 | 8 | 5 | 3 | -1 | -3 | -6 | -8 | -10 | -12 | -14 | -16 | -18 | -19 | -20 |
| 35 | 13 | 10 | 7 | 4 | 2 | -2 | -5 | -8 | -10 | -12 | -14 | -16 | -18 | -20 | -21 |
| 40 | 16 | 13 | 9 | 6 | 2 | -1 | -4 | -7 | -10 | -12 | -14 | -16 | -18 | -20 | -22 |
| 45 | 19 | 15 | 11 | 8 | 4 | 1 | -3 | -6 | -9 | -12 | -14 | -16 | -18 | -20 | -22 |
| 50 | 22 | 18 | 13 | 10 | 5 | 1 | -2 | -6 | -9 | -11 | -14 | -16 | -18 | -20 | -22 |
| 55 | 25 | 20 | 15 | 11 | 6 | 2 | -2 | -5 | -8 | -11 | -13 | -16 | -18 | -20 | -22 |
| 60 | 27 | 22 | 17 | 13 | 8 | 3 | -1 | -4 | -7 | -10 | -13 | -15 | -18 | -20 | -21 |
| 65 | 29 | 24 | 18 | 14 | 9 | 4 | 0 | -4 | -7 | -10 | -13 | -15 | -17 | -19 | -21 |
| 70 | 32 | 26 | 20 | 16 | 10 | 5 | 1 | -3 | -7 | -10 | -12 | -15 | -17 | -19 | -21 |
| 75 | 34 | 28 | 21 | 17 | 11 | 6 | 1 | -3 | -6 | -9 | -12 | -15 | -17 | -19 | -21 |
| 80 | 36 | 29 | 22 | 18 | 12 | 6 | 2 | -3 | -6 | -9 | -12 | -14 | -17 | -19 | -21 |

SYSTEMS AND METHODS FOR SENSING AN AMMONIA CONCENTRATION IN EXHAUST GASES

BACKGROUND

An ammonia ($NH_3$) sensor has been developed for monitoring exhaust gases. A drawback, however, with the ammonia sensor is that the sensor can communicate with certain exhaust gas constituents which adversely affect an accuracy of the sensor. In particular, the ammonia sensor may not accurately sense an $NH_3$ concentration in exhaust gases having water and oxygen therein.

Accordingly, the inventors herein have recognized a need for a system and methods for determining an $NH_3$ concentration in exhaust gases that minimizes and/or eliminates the above-mentioned drawback.

SUMMARY OF THE INVENTION

A method for determining an $NH_3$ concentration in exhaust gases from an engine in accordance with an exemplary embodiment is provided. The method includes generating a first signal from an $NH_3$ sensor fluidly communicating with the exhaust gases. The method further includes generating a second signal from an air humidity sensor disposed proximate to an air intake manifold of the engine indicating a humidity level. The method further includes determining an air/fuel ratio associated with the engine. The method further includes determining an $NH_3$ deviation value in a calibration table based on the second signal and the air/fuel ratio, utilizing a controller. The method further includes determining an $NH_3$ concentration value based on the first signal and the $NH_3$ deviation value, utilizing the controller. The $NH_3$ concentration value is indicative of the $NH_3$ concentration in the exhaust gases. The method further includes storing the $NH_3$ concentration value in a memory device, utilizing the controller.

A system for determining an $NH_3$ concentration in exhaust gases from an engine in accordance with another exemplary embodiment is provided. The system includes an $NH_3$ sensor fluidly communicating with the exhaust gases. The $NH_3$ sensor is configured to generate a first signal. The system further includes an air humidity sensor disposed proximate to an air intake manifold of the engine. The humidity sensor is configured to generate a second signal indicative of a humidity level. The system further includes a controller operably communicating with the $NH_3$ sensor and the humidity sensor. The controller is configured to determine an air/fuel ratio associated with the engine. The controller is further configured to determine an $NH_3$ deviation value in a calibration table based on the second signal and the air/fuel ratio. The controller is further configured to determine an $NH_3$ concentration value based on the first signal and the $NH_3$ deviation value. The $NH_3$ concentration value is indicative of the $NH_3$ concentration in the exhaust gases. The controller is further configured to store the $NH_3$ concentration value in a memory device.

A method for determining an $NH_3$ concentration in exhaust gases from an engine in accordance with another exemplary embodiment is provided. The method includes generating a first signal from an $NH_3$ sensor fluidly communicating with the exhaust gases. The method further includes retrieving an $NH_3$ deviation value for engine operation in a predetermined climate zone, utilizing a controller. The $NH_3$ deviation value is associated with a predetermined air/fuel ratio and a predetermined humidity level. The method further includes determining an $NH_3$ concentration value based on the first signal and the $NH_3$ deviation value, utilizing the controller. The $NH_3$ concentration value is indicative of the $NH_3$ concentration in the exhaust gases. The method further includes storing the $NH_3$ concentration value in a memory device, utilizing the controller.

A system for determining an $NH_3$ concentration in exhaust gases from an engine in accordance with another exemplary embodiment is provided. The system includes an $NH_3$ sensor fluidly communicating with the exhaust gases. The $NH_3$ sensor is configured to generate a first signal. The system further includes a controller operably communicating with the $NH_3$ sensor. The controller is configured to retrieve an $NH_3$ deviation value for engine operation in a predetermined climate zone. The $NH_3$ deviation value is associated with a predetermined air/fuel ratio and a predetermined humidity level. The controller is further configured to determine an $NH_3$ concentration value based on the first signal and the $NH_3$ deviation value. The $NH_3$ concentration value is indicative of the $NH_3$ concentration in the exhaust gases. The controller is further configured to store the $NH_3$ concentration value in a memory device.

A method for determining an $NH_3$ concentration in exhaust gases from an engine in accordance with another exemplary embodiment is provided. The method includes generating a first signal from an $NH_3$ sensor fluidly communicating with the exhaust gases. The method further includes retrieving an $NH_3$ deviation value for global engine operation, utilizing the controller. The $NH_3$ deviation value is associated with a predetermined air/fuel ratio and a predetermined humidity level. The method further includes determining an $NH_3$ concentration value based on the first signal and the $NH_3$ deviation value. The $NH_3$ concentration value is indicative of the $NH_3$ concentration in the exhaust gases. The method further includes storing the $NH_3$ concentration value in a memory device, utilizing the controller.

A system for determining an $NH_3$ concentration in exhaust gases from an engine in accordance with another exemplary embodiment is provided. The system includes an $NH_3$ sensor fluidly communicating with the exhaust gases. The $NH_3$ sensor is configured to generate a first signal. The system further includes a controller operably communicating with the $NH_3$ sensor. The controller is configured to retrieve an $NH_3$ deviation value for global engine operation. The $NH_3$ deviation value is associated with a predetermined air/fuel ratio and a predetermined humidity level. The controller is further configured to determine an $NH_3$ concentration value based on the first signal and the $NH_3$ deviation value. The $NH_3$ concentration value is indicative of the $NH_3$ concentration in the exhaust gases. The controller is further configured to store the $NH_3$ concentration value in a memory device.

BRIEF DESCRIPTION OF THE DRAWINGS

FIG. 5 is a schematic of another calibration table that could be utilized by the system of FIG. 1;

FIG. 6 is a schematic of another calibration table that could be utilized by the system of FIG. 1;

DETAILED DESCRIPTION OF EXEMPLARY EMBODIMENTS

Figure 1:
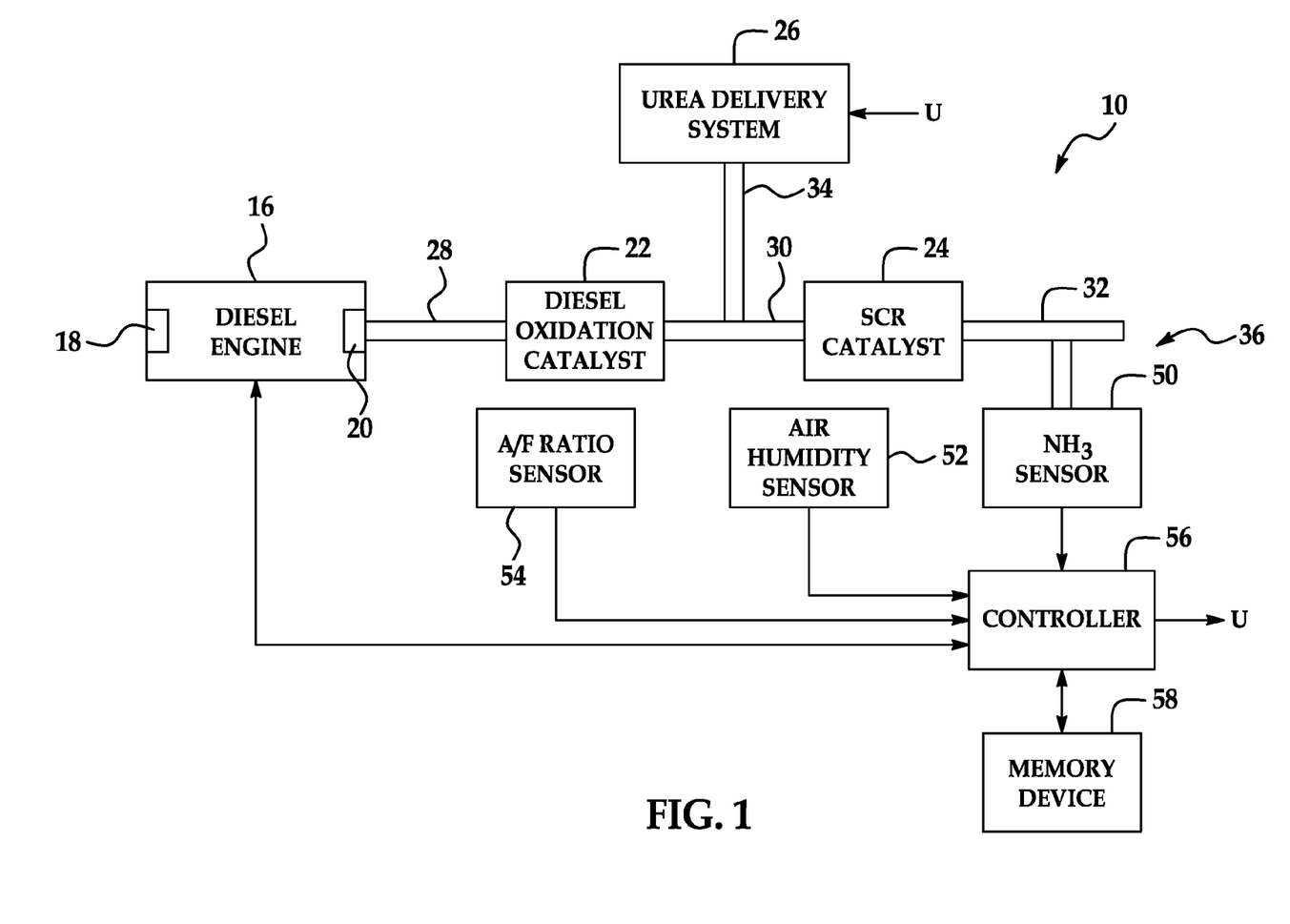
FIG. 1 is a schematic of a vehicle having a system for determining an $NH_3$ concentration in exhaust gases in accordance with an exemplary embodiment.

Referring to FIG. 1, a vehicle 10 is illustrated. The vehicle 10 has a diesel engine 20, a diesel oxidation catalyst 22, an SCR catalyst 44, a urea delivery system 26, exhaust pipes 28, 30, 32, 34, and a control system 36. An advantage of the control system 36 is that the system 36 can accurately determine an $NH_3$ concentration in exhaust gases emitted from the diesel engine 20 when excess water and oxygen is present in the exhaust gases.

The diesel engine 20 receives air in an air intake manifold 18 and combusts an air-fuel mixture therein. Thereafter, the diesel engine 20 routes exhaust gases from an exhaust manifold 20 through the exhaust pipe 28 to the diesel oxidation catalyst 22. The diesel oxidation catalyst 22 converts CO in the exhaust gases to $CO_2$. Thereafter, the exhaust gases flow from the diesel oxidation catalyst 22 through the exhaust pipe 30 to the SCR catalyst 24. The SCR catalyst 24 reduces $CO_2$ and $NO_2$ in the exhaust gases utilizing urea from the urea delivery system 26. Thereafter, the exhaust gases flow from the SCR catalyst 24 through the exhaust pipe 32 to ambient atmosphere.

The control system 36 is provided to determine an $NH_3$ concentration in exhaust gases from the diesel engine 16. Further, the control system 36 is provided to control operation of the diesel engine 16 and of the urea delivery system 26. The control system 36 includes an $NH_3$ sensor 50, an air humidity sensor 52, an air-fuel ratio sensor 54, a controller 56, and a memory device 58.

Figure 2:
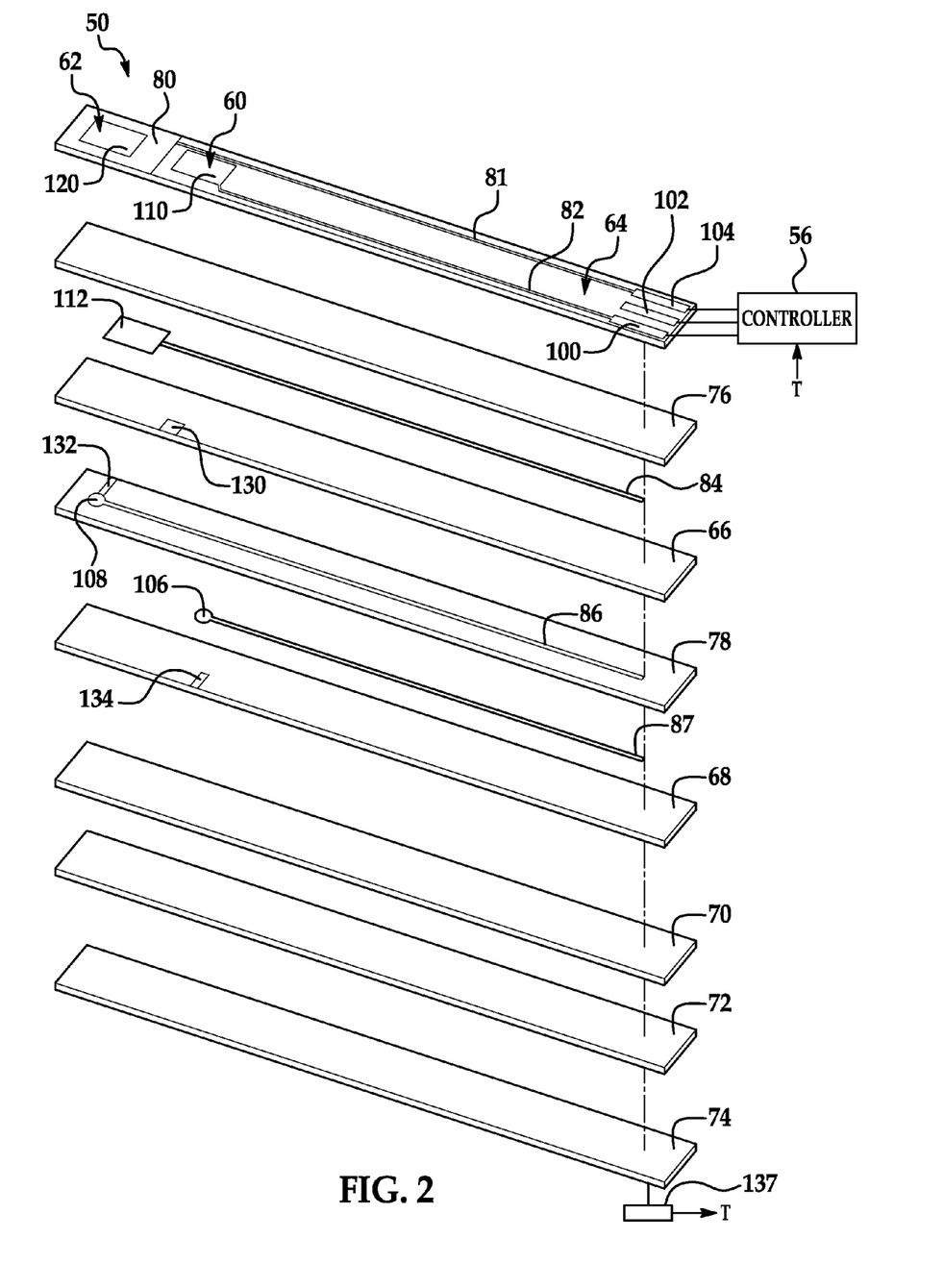
FIG. 2 is a schematic of a $NH_3$ sensor utilized by the system of FIG. 1.

Referring to FIGS. 1 and 2, the $NH_3$ sensor 50 is operably coupled to the exhaust pipe 32. The $NH_3$ sensor 50 is configured to generate a signal that is indicative of an $NH_3$ concentration in exhaust gases emitted from the diesel engine 16, which is received by the controller 56. In one exemplary embodiment, the $NH_3$ sensor 50 is further configured to generate a voltage indicative of a $NO_x$ concentration in exhaust gases downstream of the diesel oxidation catalyst 22. The $NH_3$ sensor 50 includes a $NO_x$ sensing cell 60, a $NH_3$ sensing cell 62, insulating layers 64, 66, 68, 70, 72, 74, an electrolyte layer 76, an active layer 78, a current collector 80, electrical leads 81, 82, 84, 86, 87, contact pads 100, 102, 104, electrodes 106, 108, and a contact pad 137.

The $NH_3$ sensing cell 62 is provided to generate a voltage indicative of a $NH_3$ concentration in exhaust gases communicating with the $NH_3$ sensing cell 62. The $NH_3$ sensing cell 62 includes a $NH_3$ sensing electrode 120, the reference electrode 112, and the electrolyte layer 76. The $NH_3$ sensing electrode 120 is disposed on a current collector 80 which is further disposed on the portion of the top surface of the insulating layer 64. The $NH_3$ sensing electrode 120 is electrically coupled via the electrical lead 82 the contact pad 104. The general function of the $NH_3$ sensing electrode 120 includes $NH_3$ sensing capability (e.g., catalyzing $NH_3$ gas to produce an electromotive force (emf)), electrical conducting capability (conducting electrical current produced by the emf), and gas diffusion capability (providing sufficient open porosity so that gas can diffuse throughout the electrode and to the interface region of the $NH_3$ sensing electrode 120 and the electrolyte layer 76). The $NH_3$ sensing electrode 120 can be constructed from first oxide compounds of vanadium (V), tungsten (W), and molybdenum (Mo), as well as combinations comprising at least one of the foregoing, which can be doped with second oxide components, which can increase the electrical conductivity or enhance the $NH_3$ sensing sensitivity and/or $NH_3$ sensing selectivity to the first oxide components. Exemplary first components include the ternary vanadate compounds such as bismuth vanadium oxide ($BiVO_4$), copper vanadium oxide ($Cu_2(VO_3)_2$), ternary oxides of tungsten, and/or ternary molybdenum ($MoO_3$), as well as combinations comprising at least one of the foregoing. Exemplary second component metals include oxides such as alkali oxides, alkali earth oxides, transition metal oxides, rare earth oxides, and oxides such as $SiO_2$, $ZnO$, $SnO$, $PbO$, $TiO_2$, $In_2O_3$, $Ga_2O_3$, $Al_2O_3$, $GeO$, and $Bi_2O_3$, as well as combinations comprising at least one of the foregoing. The $NH_3$ electrode material can also include traditional oxide electrolyte materials such as zirconia, doped zirconia, ceria, doped ceria, or $SiO_2$, $Al_2O_3$ and the like, e.g., to form porosity and increase the contact area between the $NH_3$ electrode material and the electrolyte. Additives of low soft point glass frit materials can be added to the electrode materials as binders to bind the electrode materials to the surface of the electrolyte. Further examples of $NH_3$ sensing electrode materials can be found in U.S. patent Ser. No. 10/734,018, to Wang et al., and commonly assigned herewith.

The $NO_x$ sensing cell 60 is provided to generate a voltage indicative of a $NO_x$ concentration in exhaust gases communicating with the $NO_x$ sensing cell 60. The $NO_x$ sensing cell 60 includes a $NO_x$ sensing electrode 110, a reference electrode 112, and the electrolyte layer 76. The $NO_x$ electrode 100 is disposed on the top surface of the insulating layer 64 and is electrically coupled via the electrical lead 82 to the contact pad 100. The electrolyte layer 76 is disposed between a bottom surface of the insulating layer 64 and a top surface of the insulating layer 66. The reference electrode 112 is disposed on a top surface of the insulating layer 66, which is disposed adjacent a bottom surface of the electrolyte layer 76. The reference electrode 112 is electrically coupled via the electrical lead 84 to the contact pad 102. The general function of the $NO_x$ sensing electrode 110 include, $NO_x$ sensing capability (e.g., catalyzing $NO_x$ gas to produce an emf), electrical conducting capability (conducting electrical current produced by the emf), and gas diffusion capability (providing sufficient open porosity so that gas can diffuse throughout the electrode and to the interface region of the electrode and electrolyte). The $NO_x$ sensing electrode 110 can be constructed from oxides of ytterbium, chromium, europium, erbium, zinc, neodymium, iron, magnesium, gadolinium, terbium, chromium, as well as combinations comprising at least one of the foregoing, such as $YbCrO_3$, $LaCrO_3$, $ErCrO_3$, $EuCrO_3$, $SmCrO_3$, $HoCrO_3$, $GdCrO_3$, $NdCrO_3$, $TbCrO_3$, $ZnFe_2O_4$, $MgFe_2O_4$, and $ZnCr_2O_4$, as well as combinations comprising at least one of the foregoing. Further, the NOx sensing electrode 110 can comprise dopants that enhance the material(s)' NOx sensitivity and selectivity and electrical conductivity at the operating temperature. These dopants can include one or more of the following elements: Ba (barium), Ti (titanium), Ta (tantalum), K (potassium), Ca (calcium), Sr (strontium), V (vanadium), Ag (silver), Cd (cadmium), Pb (lead), W (tungsten), Sn (tin), Sm (samarium), Eu (europium), Er (Erbium), Mn (manganese), Ni (nickel), Zn (zinc), Na (sodium), Zr (zirconium), Nb (niobium), Co (cobalt), Mg (magnesium), Rh (rhodium), Nd (neodymium), Gd (gadolinium), and Ho (holmium), as well as combinations comprising at least one of the foregoing dopants.

The insulating layer 66 is disposed between the electrolyte layer 76 and the active layer 78. The insulating layer 66 includes an inlet 130 extending therethrough for communicating exhaust gases to the reference electrode 112. The insulating layer 66 can be constructed from a dielectric material such as alumina.

The active layer 78 is disposed between the insulating layer 66 and the insulating layer 68. The electrode 108 is disposed on the top surface of the active layer 78 and is disposed adjacent an inlet 132 extending through the active layer 78. The inlet 132 is in fluid communication with the inlet 130 in the insulating layer 66. The electrode 108 is electrically coupled to an electrical lead 86 which is further electrically coupled to the contact pad 102. The active layer 78 can be constructed from a dielectric material such as alumina.

The insulating layer 68 is disposed between the active layer 78 and the insulating layer 70. The insulating layer 68 can be constructed from a dielectric material such as alumina. The insulating layer 68 has an inlet 134 extending therethrough that is in fluid communication with the inlet 132 of the active layer 78. The electrode 106 is disposed on a top surface of the insulating layer 68 and is electrically coupled via the electrical lead 87 to the contact pad 137. The electrode 106 generates a signal (T) indicative of a temperature of exhaust gases communicating with the NH$_3$ sensor 50 that is received by the controller 56.

The insulating layer 70 is disposed between the insulating layer 68 and the insulating layer 72. The insulating layer 70 can be constructed from a dielectric material such as alumina.

The insulating layer 72 is disposed between the insulating layer 68 and the insulating layer 74. The insulating layers 72 and 74 can be constructed from a dielectric material such as alumina.

The contact pads 100, 102, 104 are disposed on the top surface of the insulating layer 64. A voltage between the contact pads 100, 102 is indicative of a NO$_x$ concentration in exhaust gases communicating with the sensor 50. A voltage between the contact pads 104 and 102 is indicative of a NH$_3$ concentration in exhaust gases communicating with the sensor 50.

Referring to FIG. 2, the NH$_3$ sensor 50 operates based on a non-equilibrium electrochemical principle. As discussed above, the NH$_3$ sensor 50 has the NH$_3$ sensing cell 62 having the NH$_3$ sensing electrode 120, the electrolyte layer 76 and the reference electrode 112. The NH$_3$ sensing cell 62 outputs a voltage or emf that is proportional to the logarithms of a partial pressure of ammonia. The NH$_3$ sensor 50, however, has cross interference effects from water and oxygen in the exhaust gases. At a junction of the NH$_3$ sensing electrode 120 and the oxide-conducting electrolyte layer 76 is a double layer of charges, which supports an internal electric field and balances the exchange-charge currents described in the following two parallel half electrochemical reactions:

$$\frac{1}{2}O_2 + 2e \rightarrow O^= \quad (1)$$

$$O^= + \frac{2}{3}NH_3 \leftarrow N_2 + H_2O + 2e$$

The balance of the exchange-charge current densities gives an equation of:

$$J_{O2}^0 \sqrt{P_{O2}}\, e^{(-\Psi \frac{e}{kT})} = J_{NH3}^0 \left( \frac{\sqrt[2/3]{P_{NH3}}}{P_{H2O}} \right) e^{(\frac{\Psi e}{kT})} \quad (2)$$

in which k is the Botzmann constant and T is absolute temperature of the reaction system. Therefore, between the NH$_3$ sensing electrode 120 and the platinum reference electrode 112 an emf is generated which is described utilizing the following equation:

$$\mathrm{emf} = \quad (3)$$
$$(kT/3e)\mathrm{Ln}(P_{NH3}) - (kT/4e)\mathrm{Ln}(P_{O2}) - (kT/2e)\mathrm{Ln}(P_{H2O}) + \mathrm{emf}_0$$

$$\mathrm{emf}_0 = (kT/2e)\mathrm{Ln}\left(\frac{J_{NH3}^0}{J_{O2}^0}\right)$$

Based on Equation 3, the NH$_3$ concentration (or partial pressure of NH$_3$) converted from emf can be expressed as, $$\mathrm{NH}_3[\mathrm{PPM}] = A + B \cdot \exp\left[ C \cdot \left( \mathrm{emf} + \frac{kT}{4e}\mathrm{Ln}\left(\frac{P_{O2}}{P_{O2}^2}\right) + \frac{kT}{2e}\mathrm{Ln}\left(\frac{P_{H2O}}{P_{H2O}^0}\right) \right) \right] \quad (4)$$

$$B = \exp\left[ C \cdot \mathrm{emf}_0 + \frac{kT}{4e}\mathrm{Ln}(P_{O2}^0) + \frac{kT}{2e}\mathrm{Ln}(P_{H2O}^0) \right]$$

$$C = \frac{3e}{kT}$$

In Equation 4, A is the zero-adjustment constant, B is the pre-exponent constant, C is the exponent factor constant, P$_{O2}$ is a partial pressure of oxygen, P$_{H2O}$ is a partial pressure of H$_2$O, T is an absolute temperature of exhaust gases, and k is the Botzmann constant.

Based on Equations 3 and 4, the water and oxygen in exhaust gases will influence the output emf of the NH$_3$ sensing cell 62. The oxygen is residual oxygen from the inducted air after a combustion event of the diesel engine 16. The water is from both the air humidity and the combustion of diesel fuel. The oxygen and the fuel-generated water is a function of an air-fuel ratio of the combustion events and the concentrations of oxygen and water can be calculated as function of an air-fuel ratio based on a theoretical combustion model. The water from the air humidity can be measured by the air humidity sensor 52. Given a specific air humidity level and an air-fuel ratio, the emf output of the NH$_3$ sensing cell 62 will have a specific emf deviation for any given NH$_3$ concentration.

Referring to FIG. 1, the air humidity sensor 52 is operably coupled to the air intake manifold 18 of the diesel engine 16. The air humidity sensor 52 is configured to generate a signal that is indicative of humidity level of air inducted into the diesel engine 16, which is received by the controller 56.

The air-fuel ratio sensor 54 is configured to generate a signal indicative of an air fuel ratio in the diesel engine 16. In one exemplary embodiment, the air-fuel ratio sensor 54 is operably coupled to the exhaust pipe 28. In another exemplary embodiment, the air-fuel ratio sensor 54 is operably coupled to the exhaust pipe 30. In yet another exemplary embodiment, the air-fuel ratio sensor 54 is operably coupled to the exhaust pipe 32. In yet another exemplary embodiment, the controller 56 can determine an air-fuel ratio based on a calculated amount of fuel to be delivered to the diesel engine 16, where the signal from the air-fuel ratio sensor 54 would not be needed.

The controller 56 is provided to determine an $NH_3$ concentration in exhaust gases from the diesel engine 16 based on signals from the $NH_3$ sensor 50, the air humidity sensor 52, and the air-fuel ratio sensor 54. Further, the controller 56 is provided to control operation of the diesel engine 16 and of the urea delivery system 26. The controller 56 is operably coupled to the ammonia sensor 50, the air humidity sensor 52, the air-fuel ratio sensor 54, and a memory device 58. The memory device 58 is configured to store data and values utilized by the controller 56.

Figure 3:
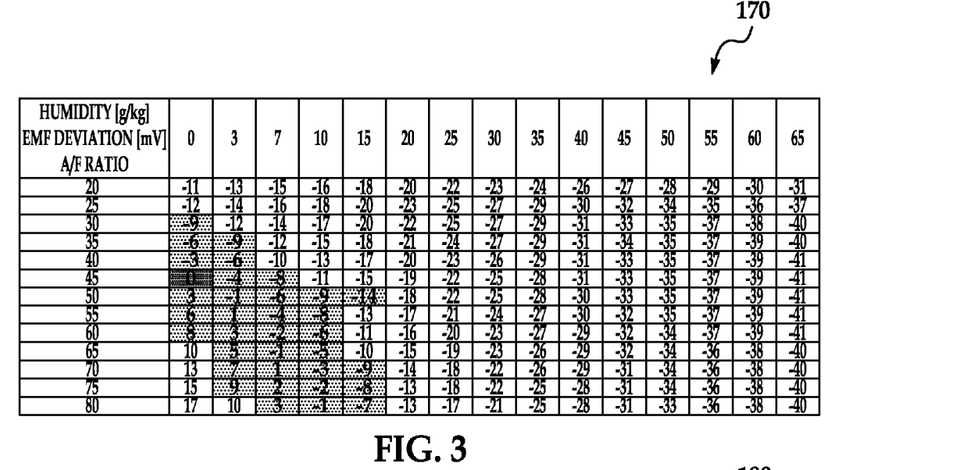
FIG. 3 is a schematic of a calibration table utilized by the system of FIG. 1.

Referring to FIG. 3, before providing a detailed explanation of an exemplary method for determining a $NH_3$ concentration in exhaust gases, an overview of a calibration table 170 will be explained. In the calibration table 170, the air-fuel ratio ranges from 20 to 80, air humidity ranges from 0 to 65 g/kg, and $NH_3$ deviation values. In one exemplary embodiment, a reference point is chosen at a humidity level equal to 0 g/kg and an air-fuel ratio equal to 45 (e.g., an exemplary calibration point for a vehicle operated at a northern arctic region). This means that if the $NH_3$ sensing cell 62 is calibrated at the humidity level equal to 0 g/kg and at an air-fuel ratio equal to 45 for a specific $NH_3$ concentration and generates a corresponding emf, then at any other air humidity level and air-fuel ratio, the emf reading of the $NH_3$ sensing cell 62 at the same $NH_3$ concentration will be the original emf value plus the $NH_3$ deviation value in millivolts shown in calibration table 170. Therefore, the calibration table 170 can be utilized to correct the cross-sensitivity effect of a humidity level and an air-fuel ratio on the outputted emf of the $NH_3$ sensing cell 62 if the humidity level and the air-fuel ratio are determined.

Thus, in one exemplary embodiment, the $NH_3$ sensing cell 62 is calibrated at a specific air-fuel ratio a specific humidity level. The obtained emf values from the $NH_3$ sensing cell 62 are linearly fitted with Equation 4 utilizing techniques known to those skilled in the art. The linear fitting allows the determination of the constants A, B and C in the Equation 4. Afterward, the emf output by the $NH_3$ sensing cell 62 at any air-fuel ratio and air humidity level can be corrected by adding the $NH_3$ deviation value in calibration table 170 to the emf output by the $NH_3$ sensing cell 62 to obtain a corrected emf. Thereafter, the controller 56 can calculate a $NH_3$ concentration value using the Equation 4 to convert the corrected emf to a $NH_3$ concentration value in parts-per-million (ppm). In one exemplary embodiment, the accuracy of the $NH_3$ sensing cell 62 is +/−2.5 ppm (5 ppm) at 10 ppm of $NH_3$ for $NH_3$ in diesel exhaust gases.

Figure 4:
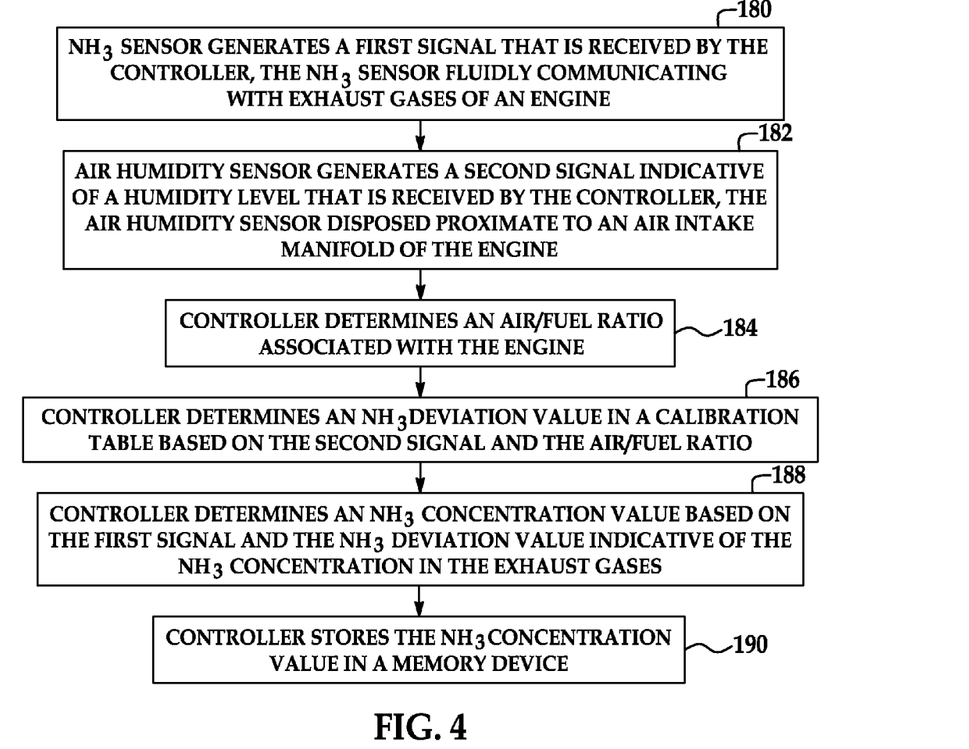
FIG. 4 is a flowchart of a method for determining an $NH_3$ concentration in exhaust gases, in accordance with another exemplary embodiment.

Referring to FIG. 4, a flowchart of a method for determining an $NH_3$ concentration in exhaust gases from the diesel engine 16 in accordance with another exemplary embodiment will now be explained. The method utilizes the calibration table 170.

At step 180, the $NH_3$ sensor 50 generates a first signal that is received by the controller 56. The $NH_3$ sensor 50 fluidly communicates with exhaust gases of the diesel engine 16.

At step 182, the air humidity sensor 52 generates a second signal indicative of a humidity level that is received by the controller 56. The air humidity sensor 52 is disposed proximate to the air intake manifold 18 of the diesel engine 16.

At step 184, the controller 56 determines an air/fuel ratio associated with the diesel engine 16. In one exemplary embodiment, the controller 56 determines the air/fuel ratio based on a signal from the air-fuel ratio sensor 54.

At step 186, the controller 56 determines an $NH_3$ deviation value in the calibration table 170 based on the second signal and the air/fuel ratio.

At step 188, the controller 56 determines an $NH_3$ concentration value based on the first signal and the $NH_3$ deviation value. The $NH_3$ concentration value is indicative of the $NH_3$ concentration in the exhaust gases.

At step 190, the controller 56 stores the $NH_3$ concentration value in the memory device 58.

Referring to FIGS. 5 and 6, before providing a detailed explanation of another exemplary method for determining a $NH_3$ concentration in exhaust gases, an overview of the calibration tables 200 and 202 will be provided.

In one exemplary embodiment, for cold climate regions, the calibration table 200 illustrates exemplary air-fuel ratio ranges from 20 to 80, the specific air humidity ranges from 0 to 65 g/kg, and $NH_3$ deviation values. Further, one operating point is selected from the table 200 for the determining a $NH_3$ deviation value for the cold climate region. For example, the operating point corresponding to an air-fuel ratio equal to 35 and a humidity level equal to 3 g/kg could be selected for the cold climate region (e.g., a region in a northern part of Europe, Asia, and America). A corrected emf of the $NH_3$ sensing cell 62 can be calculated by adding the $NH_3$ deviation value shown at the selected operating point in the calibration table 200 to the original emf of the $NH_3$ sensing cell 62. Further, an $NH_3$ concentration value can be calculated utilizing the Equation 4 with the corrected emf.

In another exemplary embodiment, for hot climate regions, the calibration table 202 illustrates exemplary air-fuel ratio ranges from 20 to 80, the specific air humidity ranges from 0 to 65 g/kg, and $NH_3$ deviation values. Further, one operating point is selected from the table 202 for the determining a $NH_3$ deviation value for the hot climate region. For example, the operating point corresponding to an air-fuel ratio equal to 45 and a humidity level equal to 20 g/kg could be selected for the hot and humid climate region (e.g., a region in a southern part of Asia, or the Amazon area of South America). A corrected emf of the $NH_3$ sensing cell 62 can be calculated by adding the $NH_3$ deviation value (in millivolts) shown at the selected operating point in the calibration table 202 to the original emf of the $NH_3$ sensing cell 62. Further, an $NH_3$ concentration value can be calculated utilizing the Equation 4 with the corrected emf.

Figure 7:
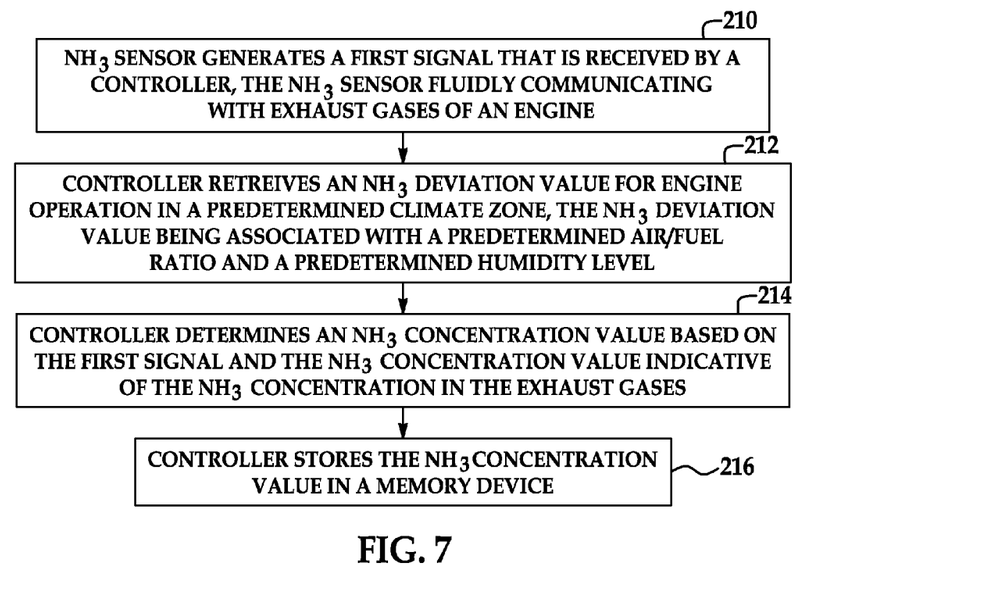
FIG. 7 is a flowchart of another method for determining an $NH_3$ concentration in exhaust gases, in accordance with another exemplary embodiment.

Referring to FIG. 7, a flowchart of a method for determining an $NH_3$ concentration in exhaust gases from the diesel engine 16 in accordance with another exemplary embodiment will now be explained. The method utilizes one of the calibration tables 200 and 202.

At step 210, the $NH_3$ sensor 50 generates a first signal that is received by the controller 56. The $NH_3$ sensor 50 fluidly communicates with exhaust gases of the engine 16.

At step 212, the controller 56 retrieves an $NH_3$ deviation value for engine operation in a predetermined climate zone. In one exemplary embodiment, the controller 56 retrieves the $NH_3$ deviation value for engine operation in a predetermined cold climate zone from the calibration table 200. In another exemplary embodiment, the controller 56 retrieves the $NH_3$ deviation value for engine operation in a predetermined hot climate zone from the calibration table 202. The $NH_3$ deviation value is associated with a predetermined air/fuel ratio and a predetermined humidity level.

At step 214, the controller 56 determines an $NH_3$ concentration value based on the first signal and the $NH_3$ deviation value. The $NH_3$ concentration value is indicative of the $NH_3$ concentration in the exhaust gases.

At step 216, the controller 56 stores the $NH_3$ concentration value in the memory device 58.

Figure 8:
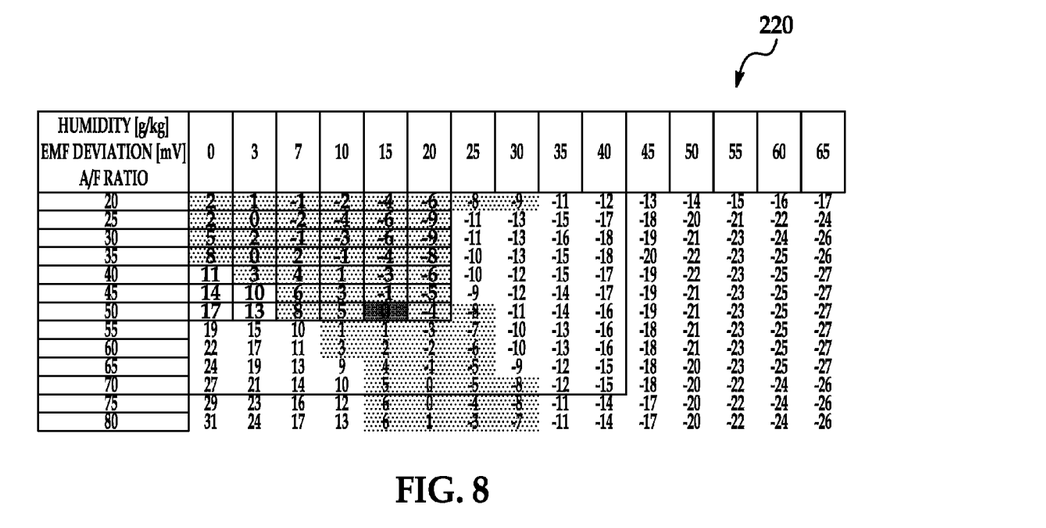
FIG. 8 is a schematic of another calibration table that could be utilized by the system of FIG. 1.

Referring to FIG. 8, before providing a detailed explanation of another exemplary method for determining a $NH_3$ concentration in exhaust gases, an overview of the calibration table 220 will be provided.

In one exemplary embodiment, the calibration table 220 illustrates exemplary air-fuel ratio ranges from 20 to 80, the specific air humidity ranges from 0 to 65 g/kg, and $NH_3$ deviation values for global engine operation. Further, one operating point is selected from the table 220 for the determining a $NH_3$ deviation value for global engine operation. For example, the operating point corresponding to an air-fuel ratio equal to 50 and a humidity level equal to 15 g/kg could be selected (e.g., an exemplary calibration point for a general climate area). A corrected emf of the $NH_3$ sensing cell 62 can be calculated by adding the $NH_3$ deviation value shown at the selected operating point in the calibration table 220 to the original emf of the $NH_3$ sensing cell 62. Further, an $NH_3$ concentration value can be calculated utilizing the Equation 4 with the corrected emf.

Figure 9:
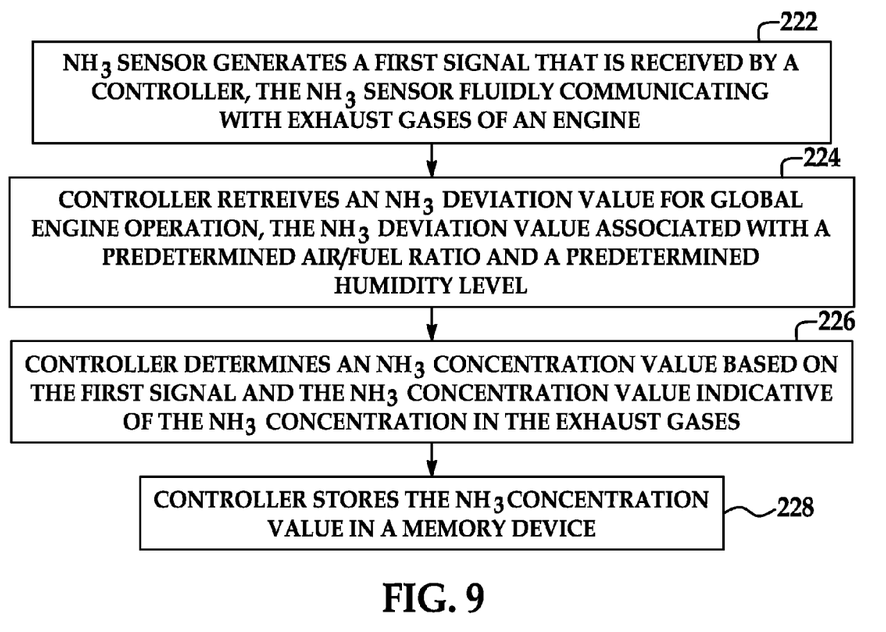
FIG. 9 is a flowchart of another method for determining an $NH_3$ concentration in exhaust gases, in accordance with another exemplary embodiment.

Referring to FIG. 9, a flowchart of a method for determining an $NH_3$ concentration in exhaust gases from the diesel engine 16 in accordance with another exemplary embodiment will now be explained. The method utilizes the calibration table 220.

At step 222, the $NH_3$ sensor 50 generates a first signal that is received by the controller 56. The $NH_3$ sensor 50 fluidly communicates with exhaust gases of the engine 16.

At step 224, the controller 56 retrieves an $NH_3$ deviation value for global engine operation. The $NH_3$ deviation value is associated with a predetermined air/fuel ratio and a predetermined humidity level.

At step 226, the controller 56 determines an $NH_3$ concentration value based on the first signal and the $NH_3$ deviation value. The $NH_3$ concentration value is indicative of the $NH_3$ concentration in the exhaust gases.

At step 228, the controller 56 stores the $NH_3$ concentration value in the memory device 58.

The systems and methods for determining an $NH_3$ concentration in exhaust gases from an engine provide a substantial advantage over other systems and methods. In particular, one exemplary system and method provide a technical effect of accurately determining $NH_3$ concentrations in exhaust gases based on an air-fuel ratio and a humidity level.

While embodiments of the invention are described with reference to the exemplary embodiments, it will be understood by those skilled in the art that various changes may be made and equivalents may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling within the scope of the intended claims. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

What is claimed is:

1. A method for determining an $NH_3$ concentration in exhaust gases from an engine, comprising:
   generating a first signal from an $NH_3$ sensor fluidly communicating with the exhaust gases;
   generating a second signal from an air humidity sensor disposed proximate to an air intake manifold of the engine indicating a humidity level;
   determining an air/fuel ratio associated with the engine;
   determining an $NH_3$ deviation value in a calibration table based on the second signal and the air/fuel ratio, utilizing a controller;
   determining an $NH_3$ concentration value based on the first signal and the $NH_3$ deviation value, utilizing the controller, the $NH_3$ concentration value indicative of the $NH_3$ concentration in the exhaust gases; and
   storing the $NH_3$ concentration value in a memory device, utilizing the controller.

2. The method of claim 1, wherein determining an air/fuel ratio associated with the engine comprises:
   generating a third signal from an air-fuel ratio sensor fluidly communicating with the exhaust gases; and
   determining the air/fuel ratio based on the third signal, utilizing the controller.

3. The method of claim 1, wherein the $NH_3$ sensor is an electrochemical cell $NH_3$ sensor.

4. A system for determining an $NH_3$ concentration in exhaust gases from an engine, comprising:
   an $NH_3$ sensor fluidly communicating with the exhaust gases, the $NH_3$ sensor configured to generate a first signal;
   an air humidity sensor disposed proximate to an air intake manifold of the engine, the humidity sensor configured to generate a second signal indicative of a humidity level;
   a controller operably communicating with the $NH_3$ sensor and the humidity sensor, the controller configured to determine an air/fuel ratio associated with the engine;
   the controller further configured to determine an $NH_3$ deviation value in a calibration table based on the second signal and the air/fuel ratio;
   the controller further configured to determine an $NH_3$ concentration value based on the first signal and the $NH_3$ deviation value, the $NH_3$ concentration value indicative of the $NH_3$ concentration in the exhaust gases; and
   the controller further configured to store the $NH_3$ concentration value in a memory device.

5. The system of claim 4, further comprising:
   an air-fuel ratio sensor fluidly communicating with the exhaust gases, the air-fuel ratio sensor configured to generate a third signal; and
   the controller configured to determine the air/fuel ratio associated with the engine based on the third signal.

6. The system of claim 4, wherein the NH3 sensor is an electrochemical cell $NH_3$ sensor.

* * * * *